(12) United States Patent
Moskal et al.

(10) Patent No.: US 6,274,314 B1
(45) Date of Patent: Aug. 14, 2001

(54) DIAGNOSTIC ASSAY FOR THE MODIFIED NUCLEOSIDES PSEUDOURIDINE, 7-METHYLADENOSINE, OR 1-METHYLADENOSINE

(75) Inventors: Joseph R. Moskal, Chicago; James F. Grutsch, Wilmette, both of IL (US)

(73) Assignee: Nyxis NeuroTherapies, Inc., Chicago, IL (US)

( * ) Notice: Subject to any disclaimer, the term of this patent is extended or adjusted under 35 U.S.C. 154(b) by 15 days.

(21) Appl. No.: 09/053,913

(22) Filed: Apr. 2, 1998

(51) Int. Cl.$^7$ .................. G01N 33/537; G01N 33/538; G01N 33/541; G01N 33/754; C12Q 11/68
(52) U.S. Cl. .................. 435/6; 424/1.49; 424/178.1; 435/7.1; 435/7.72; 435/7.94; 435/7.95; 435/7.92; 436/94; 436/63; 436/64; 436/518; 436/538; 436/541; 436/542
(58) Field of Search .................. 424/1.49, 178.1; 435/6, 7.1, 7.72, 7.92, 7.94, 7.95, 970, 971; 436/94, 63, 64, 518, 538, 541, 542, 810

(56) References Cited

U.S. PATENT DOCUMENTS

| | | | |
|---|---|---|---|
| 4,313,734 | 2/1982 | Leuvering | 435/525 |
| 4,366,241 | 12/1982 | Tom | 435/7.91 |
| 4,376,110 | * 3/1983 | David | 436/513 |
| 4,632,901 | 12/1986 | Valkirs | 435/5 |
| 4,656,448 | 4/1987 | Luetzow | 3/262 |
| 4,665,018 | * 5/1987 | Vold | 435/6 |
| 4,687,733 | 8/1987 | Trewyn | 435/7.23 |
| 4,770,853 | 9/1988 | Bernstein | 422/58 |
| 4,786,589 | 11/1988 | Rounds | 435/5 |
| 4,929,544 | * 5/1990 | Vold | 435/6 |

OTHER PUBLICATIONS

Trweyn and Grever, (1986), *CRC Crit. Rev. Clin. Lab. Sci.* 24:71–93.
Heldman, et al., (1983), *J. Lab. Clin. Med.*, 101:783–792.
Heldman, et al., (1983), *Blood.*, 61:291–296.
Heldman, et al., (1983), *J. Nat. Can. Inst.*, 71:269–273.
Rasmuson, et al., (1983), *Acta Radiolog. Oncology.*, 22:209–214.
Rasmusen and Bjork., (1985), *Bull Mol. Biol. Med.*, 10:143–154.
Tamura., (1986), *Cancer.*, 57:1571–1575.
Tamura., (1986), *Clin. Chem. Acta.*, 154:125–132.
Trewyn., (1983), *Cancer Res.*, 49:2513–2517.
Fishbein, et al., (1983), *Cancer Res.*, 43:2971–2974.
Gehrke, et al., (1978), *J. Chromatography.*, 150:455–476.
Levine, et al., (1984), *J. Nat. Cancer Inst.*, 54:341–343.
Vold, et al., (1979), *Nuc. Acids Res.*, 7:193–204.
Vold, et al., (1982), *Cancer Res.*, 42:5265–5269.
Woodsworth, et al., (1983), *Bioch. Biophys. Res.*, 114:791–796.
Farr, et al., (1958), *J. Infect. Dis.*, 103:239–262.
Muller, et al., (1980), *J. Immunol. Meth.*, 34:345–352.
Engvall, et al., *Biophys. Acta.*, 251:427–434.
Marvel, CC, et al. Altered RNA turnover in carcinogenesis. Molec. Chem. Neuropath. 21?353–368, 1994.*
Gerrits, GPJM, et al., Arginosuccinic aciduria: clinical and biochemical findings in three children with the late onset form, with special emphasis on cerebrospinal fluid findings of amino acids and pyrimidines. Neuropediatrics 24:15–18, 1993.*
Manjula, S, et al., Urinary excretion of pseudouridine in patients with brain tumours. Acta Oncologica. 32(3):311–314, 1993.*

* cited by examiner

*Primary Examiner*—David Saunders
*Assistant Examiner*—Mary Beth Tung
(74) *Attorney, Agent, or Firm*—McDonnell Boehnen Hulbert & Berghoff (57) ABSTRACT

The present invention relates to an assay for the detection of modified nucleoside levels in a patient. Detection of the modified nucleoside levels in a patient having a disease such as cancer allows for the progression of the disease to be followed and therapeutic regimens to be altered. Such an assay is particularly useful in following the response of cancer patients to chemotherapeutic treatment.

40 Claims, 4 Drawing Sheets

DIAGNOSTIC ASSAY FOR THE MODIFIED NUCLEOSIDES PSEUDOURIDINE, 7-METHYLADENOSINE, OR 1-METHYLADENOSINE

FIELD OF THE INVENTION

The present invention relates to an assay for the detection of modified nucleoside levels in a patient. Detection of the modified nucleoside levels in a patient having a disease such as cancer allows for the progression of the disease to be followed and therapeutic regimens to be altered. Such an assay is particularly useful in following the response of cancer patients to chemotherapeutic treatment.

BACKGROUND OF THE INVENTION

Ribonucleic acids (RNA) have central roles in all aspects of cellular metabolism. Protein synthesis is dependent upon the coordinated interactions of transfer RNA (tRNA), ribosomal RNA (rRNA), and messenger RNA (mRNA). The cellular roles of RNA are complex, as they function as structural elements (rRNA), catalytic components (in RNA processing), informational molecules (mRNA), and as a direct link between information contained in DNA and in proteins (tRNA). Gene activation is dependent not only on specific mRNA transcription but also on its correct splicing, capping and processing to create a functional mRNA. Consequently, in disease states such as cancer, where abnormal cell growth occurs, it is not unexpected that perturbations are indicative of metabolic alterations that can be exploited for cancer diagnosis or therapy.

RNA contains a variety of modified nucleosides, which are enzymatically modified post-transcriptionally by a variety of modification enzymes. Over 50 chemically distinct modifications have been described, each requiring a different enzyme. In humans and other animals normal RNA turnover and breakdown creates free modified nucleosides. These modified nucleosides collect in the circulation from which they are filtered and concentrated by the kidneys into the urine for excretion. Consequently, all urine contains levels of modified nucleosides that reflect RNA degradation in the organism.

Numerous reports have correlated increased rates of modified nucleoside urinary excretion with cancer and other disease states. Examples of such cancers include leukemias (Trweyn and Grever, 1986. *CRC Crit. Rev. Clin. Lab. Sci.*, 24:71–93), chronic myelogenous leukemia (Heldman, et al. 1983. *J. Lab. Clin. Med.*, 101:783–792), adult acute leukemia (Heldman, et al. 1983. *Blood*, 61:291–296), childhood acute lymphoblastic leukemia (Heldman, et al. 1983. *J. Nat. Can. Inst.*, 71:269–273), bronchogenic carcinoma (Rasmuson, et al. 1983. *Acta Radiolog. Oncology*, 22:209–214), mammary and colorectal carcinoma (Rasmusen and Bjork, 1985. *Bull. Mol. Biol. Med.*, 10:143–154), hepatocellular carcinoma (Tamura, 1986. *Cancer*, 57:1571–1575), small cell lung cancer (Tamura, 1986. *Clin. Chem. Acta*, 154:125–132) ovarian cancer (Oerlemans and Lange, 1986.), malignant lymphomas Rasmuson and Bjork, 1983.), nasopharyngeal carcinoma (Trewyn, 1982. *Cancer* 49: 2513–2517), and malignant mesothelioma (Fishbein, et al, 1983. *Cancer Res.* 43:2971–2974).

The monitoring of urinary modified nucleoside levels has not been demonstrated to be useful for cancer diagnosis, to stage disease, to determine the efficacy of a treatment protocol or to monitor recurrence of cancers in remission. The present application provides one skilled in the art with the reagents and methodologies required to efficiently measure levels of modified nucleosides in a patient as a diagnostic or predictive assay useful in designing treatment protocols.

SUMMARY OF THE INVENTION

The present invention relates to a method for detecting modified nucleosides in a biological sample such as a bodily fluid. The methods provided herein are useful for detecting a modified nucleoside such as psueouridine ($\psi$), 7-methylinosine ($m^7I$), and 1-methyladenosine ($m^1A$). It is an object of the invention to provide a method for determining the effectiveness of a treatment protocol for treating a disease such as cancer. It is a further object of the invention to provide an in vitro and an in vivo assay for determining the effectiveness of a treatment protocol for treating a disease such as cancer. It is also an object of the present invention to provide a method of diagnosing or detecting cancer.

In one embodiment, a method for determining the effectiveness of a treatment protocol comprising determining the concentration of a modified nucleoside in the biological fluid of a patient is provided.

In another embodiment, an assay is provided wherein the effectiveness of a particular treatment protocol may be determined in vitro using a cell line or primary tumor cells or in vivo using an animal model.

In another embodiment, a method for determining the effectiveness of a treatment protocol comprising contacting a bodily fluid from a patient with a labeled antibody that is specific to a modified nucleoside and detecting the labeled antibody, thus indicating the presence of a modified nucleoside in the bodily fluid.

DETAILED DESCRIPTION OF THE INVENTION

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, $2^{nd}$ Ed.* (R. I. Freshney. 1987. Liss, Inc. New York, N.Y.), and *Gene Transfer and Expression Protocols*, pp. 109–128, ed. E. J. Murray, The Humana Press Inc., Clifton, N.J.).

The reagents and methodologies of the present invention may be utilized to prevent, detect, or treat a variety of disorders in which increased levels of modified nucleosides are produced by the affected cells. An example of such a disorder is cancer. Cancer is defined herein as any cellular malignancy for which a loss of normal cellular controls results in unregulated growth, lack of differentiation, and increased ability to invade local tissues and metastasize. Cancer may develop in any tissue of any organ at any age. Cancer may be an inherited disorder or caused by environmental factors or infectious agents; it may also result from a combination of these. For the purposes of utilizing the present invention, the term cancer includes both neoplasms and premalignant cells. A specific example of utilization of the present invention to treat brain cancer is provided herein. Brain cancer is defined herein as any cancer involving a cell of neural origin. Examples of brain cancers include but are not limited to intracranial neoplasms such as those of the skull (i.e., osteoma, hemangioma, granuloma, xanthoma, osteitis deformans), the meninges (i.e., meningioma, sarcoma, gliomatosis), the cranial nerves (i.e., glioma of the optic nerve, schwannoma), the neuroglia (i.e., gliomas) and ependyma (i.e., ependymomas), the pituitary or pineal body (i.e., pituitary adenoma, pinealoma), and those of congenital origin (i.e., craniopharygioma, chordoma, germinoma, teratoma, dermoid cyst, angioma, hemangioblastoma) as well as those of metastatic origin.

It has been shown that detection of modified nucleosides in urine is useful for diagnosis and prognostic evaluation of certain cancers such as leukemia (U.S. Pat. No. 4,687,733). It has been found that myelogenous leukemia, acute lymphoblastic leukemia and chronic myelogenous leukemia may be distinguished by determination of 1-methylinosine levels in a patient's urine (Heldman et al. 1983. *Blood* 61: 291–296; Heldman, et al. 1983. *J. Lab. Clin. Med.* 101: 783–792). The '733 patent demonstrated that detection of 1-methylinosine was positively correlated with the percentage of blast cells in a patient's bone marrow aspirate. The levels of 1-methylguanosine, pseudouridine, 1-methyladenosine, or 5-methylcytidine did not correlate with blast cell numbers. As such only measurement of 1-methylinosine was useful for providing a predictive measure of leukemia in a patient.

The present invention comprises a methodology for the detection of modified nucleosides in a biological or bodily fluid of a patient suspected of having a tumor or other biologiclal disorder in which an increased level of modified nucleosides is a result. Suitable biological or bodily fluids may include but are not limited to saliva, urine, blood, and cerebrospinal fluid. Preferred modified nucleosides for detection in an assay provided herein are psueouridine ($\psi$), 7-methylinosine ($m^7I$), and 1-methyladenosine ($m^1A$). By detecting the levels of modified nucleosides such as these in bodily fluid of a patient, the presence of a tumor such as a glioma or meningioma in that patient may be detected. In addition, the present invention may be utilized to predict the responsiveness of a patient to a particular chemotherapeutic regimen. For instance, a patient having a high level of $m^1A$ may be predicted to respond less well to a particular chemotherapeutic regimen as compared to a patient having a high level of $\psi$. As such, the treatment the patient receives may be modified to optimize the results of administration of certain drugs or other compounds.

In one embodiment of the present invention, an in vitro assay for the identification of compounds having the ability to decrease modified nucleoside excretion from tumor cells. Compounds identified in such an assay may then be tested in an in vivo model as shown below or administered to a patient for treatment of a disease such as cancer. A tumor cell line, either obtained from a commercial source such as the ATCC (Rockville, Md.), or tumor cells obtained from an excised human tumor are seeded onto a plate, such as a 6-, 12-, 24-, 48- or 96-well plate at a sufficient concentration to allow for normal cell growth in normal media. The cells of certain wells are then treated with various concentrations of a compound that may affect modified nucleoside production by the cells. Such a compound may include dibutyrate (available from Sigma Chemicals, St. Louis, Mo.) to which the cells may be exposed at $10^{-10}$ to $10^{-1}$ M concentrations. Modified nucleoside levels are then characterized using procedures reported by Gehrke et al. (*J. Chromatography*, 150: 455–476, 1978). An affinity column may used as an initial step to partially purify the ribonucleosides, but any technique known by one skilled in the art for performing such purifications may be utilized. Modified nucleosides contained in this mixture may then analyzed using a methodology such as reversed-phase high performance liquid chromatography (RP-BPLC). Modified nucleosides may then be identified by retention time using known standards and quantified by peak area integration. A compound is determined to affect modified nucleoside production by the cells if an increase or a decrease of the level of a particular modified nucleoside is detected following exposure of the cells to the compound. This information may then be extrapolated to determine the in vivo levels needed to achieve a similar modification of modified nucleoside production in a patient following dibutyrate administration in vivo.

One obstacle to the design of effective therapies for treating cancer is the variability in tumor cell responses between individuals. The assays provided herein may be utilized to specifically characterize a patient's own tumor cells with respect to the affect of compounds on modified nucleoside production. To determine the responsiveness of an individual's tumor cells to a particular treatment regimen, which may include chemotherapy, radiation therapy, immunotherapy or other anti-cancer treatment, a tumor may be resected from a patient and prepared as a primary tumor cell suspension. Isolation and preparation of the tumor cells may be performed using any of the procedures known to one skilled in the art (see for example, *Culture of Animal Cells: A Manual of Basic Technique*, $2^{nd}$ Ed. (R. I. Freshney. 1987. Liss, Inc. New York, N.Y.)). The cells may then be plated in culture dishes such as a 96-well plates at a suitable concentration (preferably $10^3$ to $5 \times 10^6$ cells/well) in normal media and treated with various concentrations of a compound that may affect modified nucleoside production by the cells. Modified nucleosides levels may then be determined as described herein. An increase or decrease in modified nucleoside levels following exposure of a patient's cells to a chemotherapeutic compound or other treatment may reflect the ability of that treatment to provide the patient with a more favorable prognosis.

This system may also be tested using an animal model wherein individual animals are inoculated with tumor cells (preferably $10^2$–$10^7$ tumor cells). The animal may comprise any animal suitable to laboratory testing, but is preferably a rat or a mouse. A nu/nu mouse ("nude mouse") may be utilized where the tumor to be tested is derived from a human. The tumor cells may have been derived from any cancer, but preferably one of the brain. The level of modified nucleoside in the bodily fluid of each animal is determined prior to inoculation. The animal is then inoculate with tumor cells and after a sufficient period of time during which the tumor may proliferate, preferably 5–20 days, biological fluid is again collected. The collected biological fluid is then tested for the levels of modified nucleosides. The animals may be treated by a treatment regimen either prior to inoculation or after inoculation with the tumor cells. The modified nucleoside concentration of the biological fluid is then determined and compared to the levels detected in untreated mice. Both sets of data may also be compared to the levels detected in healthy controls that have not been inoculated with any tumor cells. The levels of modified nucleoside detected in the biological fluid of each rat may also be correlated to tumor size and overall health of the animal. If the amount of modified nucleoside has decreased, this indicates that the particular chemotherapeutic compound is effective for treating the particular tumor type. If the levels of modified nucleoside has increased, this indicates that chemotherapeutic compound is ineffective for treating the particular tumor type. In this manner, the effectiveness of a particular treatment regimen against a tumor type can be ascertained.

It is useful in conducting such assays to have an antibody having specificity to the modified nucleosides to be detected. Polyclonal or monoclonal antibodies may be produced that have specificity for psueouridine ($\psi$), 7-methylinosine ($m^7I$), and 1-methyladenosine ($m^1A$). The generation of antibodies to 1-methylinosine is described in U.S. Pat. No. 4,687,733. A similar method may be utilized to generate antibodies to psueouridine ($\psi$), 7-methylinosine ($m^7$), and 1-methyladenosine ($m^1A$) by substituting one of these modified nucleosides for 1-methylinosine. Immunizations such as these are well known and the reagents and methodologies for such immunizations are widely available to one skilled in the art.

The present invention provides an assay for detection of modified nucleosides in a biological sample such as bodily fluid. Several techniques are available to one skilled in the art for the detection of a quantity of antigen or antibody in a biological fluid. Radioimmunoassays may be utilized as described by Levine, et al. (J. Natl. Cancer Inst. 54: 341–343, 1984), Vold, et al. (Nuc. Acids Res., 7: 193–204, 1979 and Cancer Res., 42: 5265–5269, 1982), or Woodsworth, et al. (Bioch. Biophys. Res., 114: 791–796, 1983), for example. Radioimmunoassay may be carried out as described by Farr, et al. (J. Infect. Dis. 103: 239–262, 1958) with certain modifications as described in U.S. Pat. No. 4,687,733 (and substituting $\psi$, $m^7I$, or $m^1A$ for 1-methylinosine). The affinity constants can be determined as described for the antibodies as described by Muller, et al. (J. Immunol. Meth. 34: 345–352, 1980).

Other such methods include variations of the competitive binding assay and the sandwich immunoassay. In a competitive assay, antibody bound to a solid surface is contacted with a biological sample containing an unknown antigen, and with a known quantity of antigen complexed with a detectable label. In a sandwich assay, antibody for the unknown antigen is bound to a solid surface, the antigen is reacted with the antibody, and the amount of bound antibody is measured by detection of the antigen with a second antibody bound to a detectable label. A detectable label may be a radioactive label such as $^{125}I$, a fluorometric label such as FITC or an enzyme label that causes conversion of a substrate to a colored form in a colorimatric assay.

In a typical competitive assay, such as that described by Engvall et al. (*Biochem. Biophys. Acta*, 251: 427–434), the amount of antigen is determined using an enzyme-labeled antibody and an antibody coated tube. The labeled antibody bound to the tube is contacted with a biological sample suspected of containing an antigen, and with a known quantity of antigen, thus forming an immunological complex. Following a wash step, the immunological complex is contacted with a substrate solution that changes color in the presence of the enzyme label on the antigen. The color change of the substrate is determined by measuring the absorbance of the solution at a particular wavelength. An ELISA may also be used to detect a modified nucleoside Solid phase immunoassay devices may also be utilized in practicing the present invention. A suitable solid phase immunoassay device comprises a member of a ligand-receptor pair, generally an antibody, hapten or antigen is bound to a solid support. U.S. Pat. No. 4,366,241 describes a migration type assay in which a membrane comprises, bound to it, the reagents needed to perform the assay and further comprises an analyte detection zone for identification of a target molecule. U.S. Pat. No. 4,770,853 describe other migration type devices comprising reagents attached to colored labels for direct visual detection of the assay results in the absence of additional reagents. U.S. Pat. No. 4,632, 901 illustrates a flow-through type immunoassay device comprising antibody bound to a porous membrane or filter to which is added a liquid sample. Target analyte binds to the antibody as the liquid flows through the membrane. Lableled anitbody is then added, which allows for visual detection of labeled antibody. U.S. Pat. Nos. 4,313,734, and 4,786,589 and 5,656,448 describe dipstick devices useful for detection antigens from a body fluid such as urine.

The present invention may be practiced using any of such detection devices. For instance, a dipstick comprising an antibody having specificity to a modified nucleoside bound to solid support may be inserted into a test solution comprising a biological fluid such as bodily fluid into which a labeled anti-modified nucleoside antibody has been added. The antibody bound to the dipstick and the labeled antibody are both specific for a modified nucleoside, but are specific to different epitopes. Binding of each antibody to the modified nucleoside is not mutually exclusive with respect to one another. As such, the antibody of the dipstick and the labeled antibody may bind to the modified nucleoside to form a sandwich.

To carry out this method, the dipstick, biological fluid and labeled antibody are kept in contact with one another for a sufficient period of time to allow for binding. The modified nucleoside contained within the biological test sample is captured as a complex comprising a solid support bound to an unlabelled antibody bound to a modified nucleoside, the modified nucleoside being further bound to a labeled antibody. The complex is then processed to allow detection of the labeled antibody, allowing for detection of the complex. Quantitation of the complex bound to the dipstick is then accomplished by means known to one skilled in the art. Comparison of the amount of bound modified nucleoside in a test sample is then compared to a control sample (i.e., from a tumor free patient). A greater amount of bound complex in the test sample indicates a higher level of modified nucleoside in the test biological sample.

The following non-limiting examples illustrate the inventors' preferred methods for isolating a nucleic acid molecule having the above-described properties. The following examples are provided for illustrative purposes only and are not intended, nor should they be construed, as limiting the invention in any manner. Those skilled in the art will appreciate that modifications and variations of the following examples can be made without exceeding the spirit or scope of the present invention and claims.

EXAMPLE 1

Detection of MN in Patients Having Brain Cancer

Using RP-HPLC, the concentration of three MNs (pseudouridine, 7-methylinosine, and 1-methyladenosine) in the urine of patients diagnosed with gliomas (Ghm) and meningiomas (Mng) was measured and compared that detected in non-tumor craniotomy controls (NTC) and healthy controls (HC).

To perform the assay, urine was collected pre-operatively from three groups of subjects: tumor (n=151), non-tumor craniotomy (CC; n=46) and HC (n=20) and stored at −20° C. Each subject's age, sex, tumor volume, mediaction, follow-up health and survival rate was recorded. The tumor group was subdivided into three groups: glioblastoma multiforme (GBM; n=52), medium grade glioma (MG, n=47) and meningioma (MEN, n=52). Modified nucleosides were characterized using procedures reported by Gehrke et al. (*J. Chromatography*, 150: 455–476, 1978). A phenyl-boronate affinity column was used as an initial step to partially purify the ribonucleosides. Modified nucleosides contained in this mixture were then analyzed by reversed-phase high performance liquid chromatography (RP-HPLC) using a 4×300 mm μBONDAPAK column (waters, Milford, Mass.) under the following conditions: buffer, 1% methanol in 0.01M sodium phosphate, pH 5.1; temperature, 25° C.; flow rate, 1 ml/min. Modified nucleosides were identified by retention time using known standards and quantified by peak area integration. These values were then normalized according to each patient's creatine concentration (Sigma Diagnostics Creatinine Kit; Sigma Chemicals, St. Louis, Mo.).

Figure 1A:
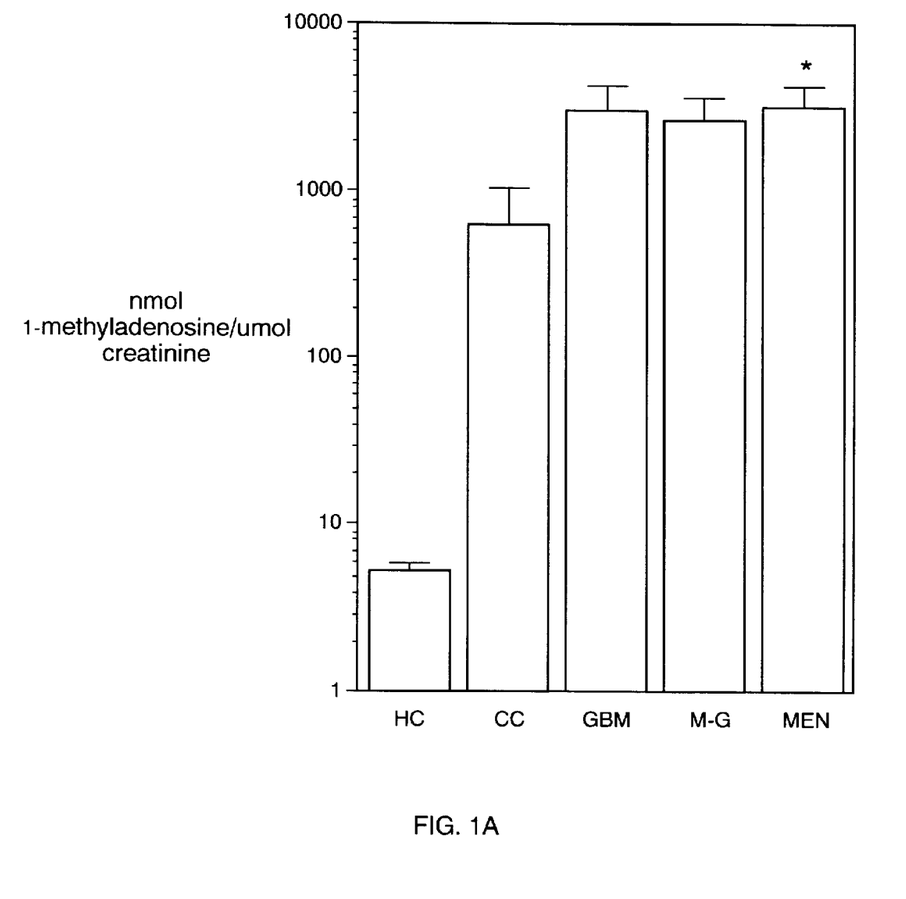
FIG. 1. Urinary 1-methyladenosine levels in patients with various cancers.
Figure 1B:
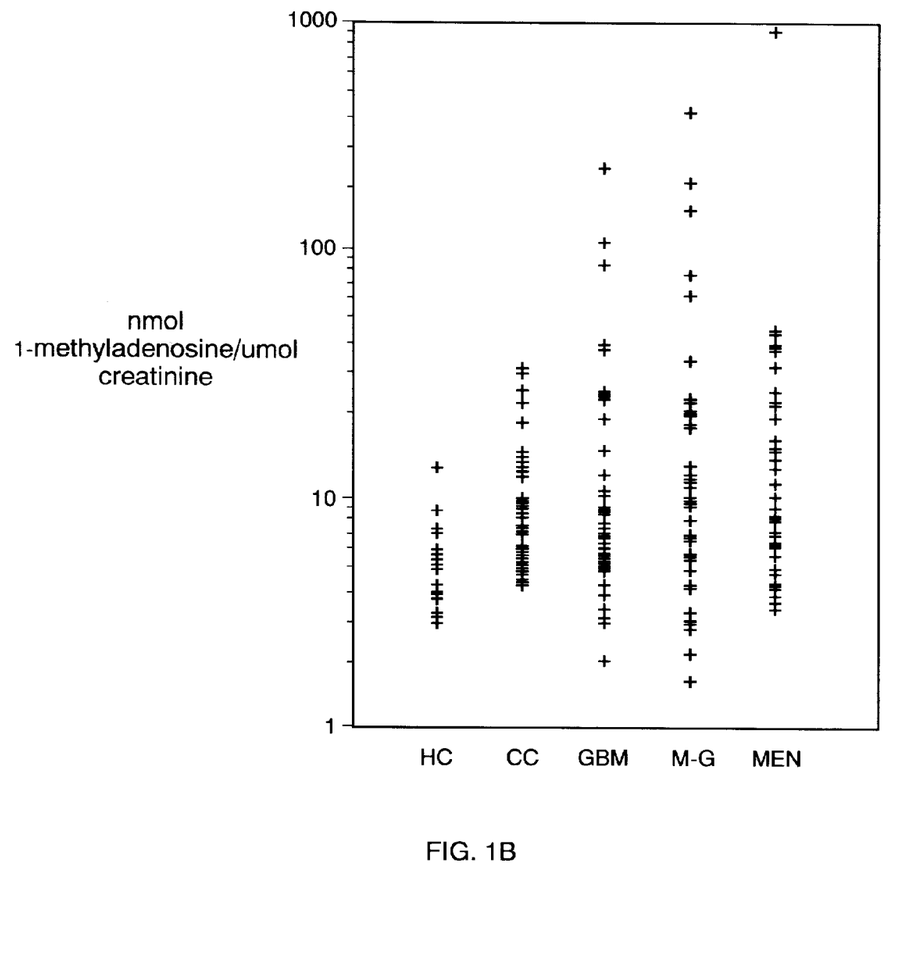
Figure 2:
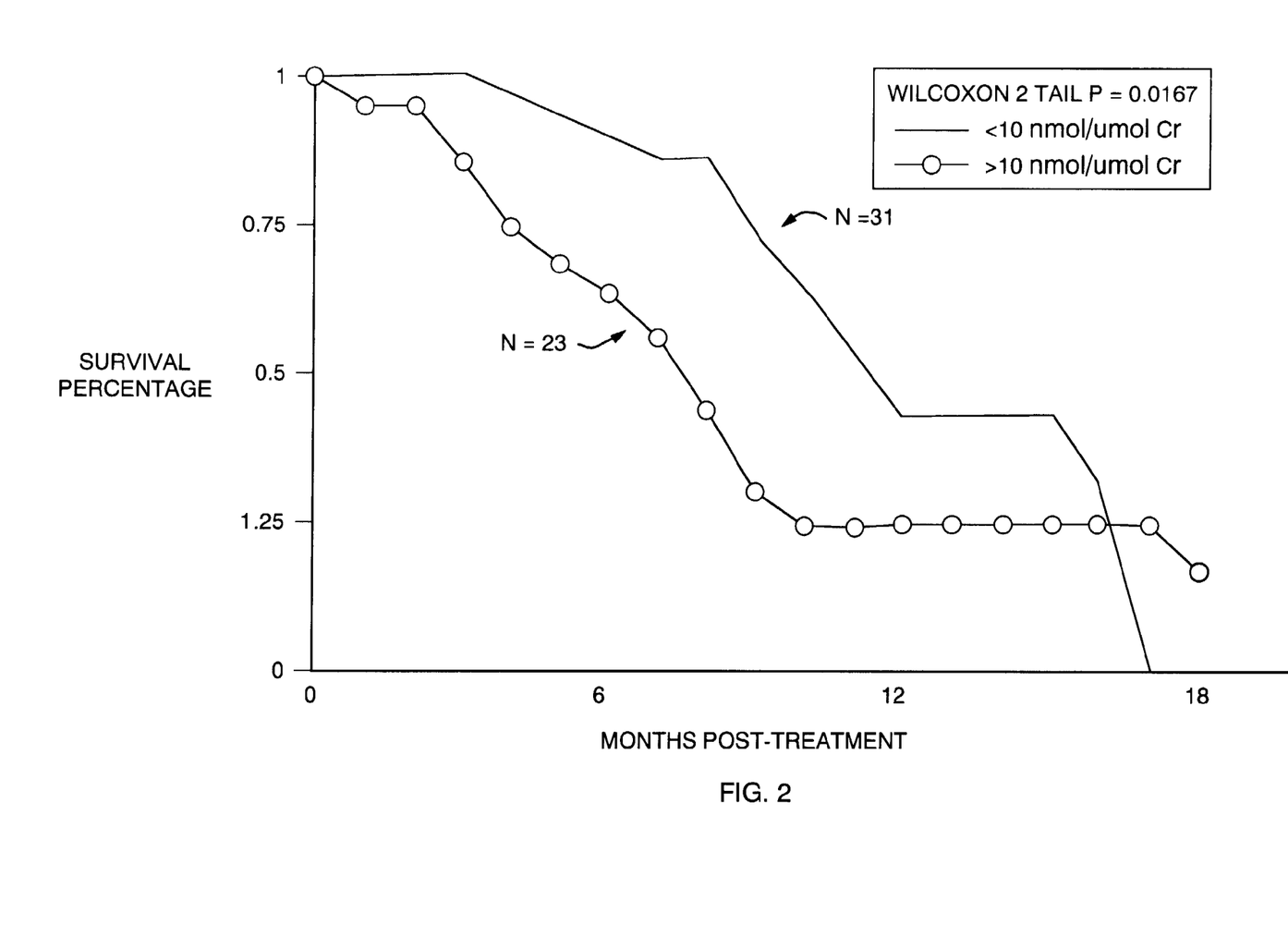
FIG. 2. GBM survival relates to 1-methyladenosine levels.
Figure 3:
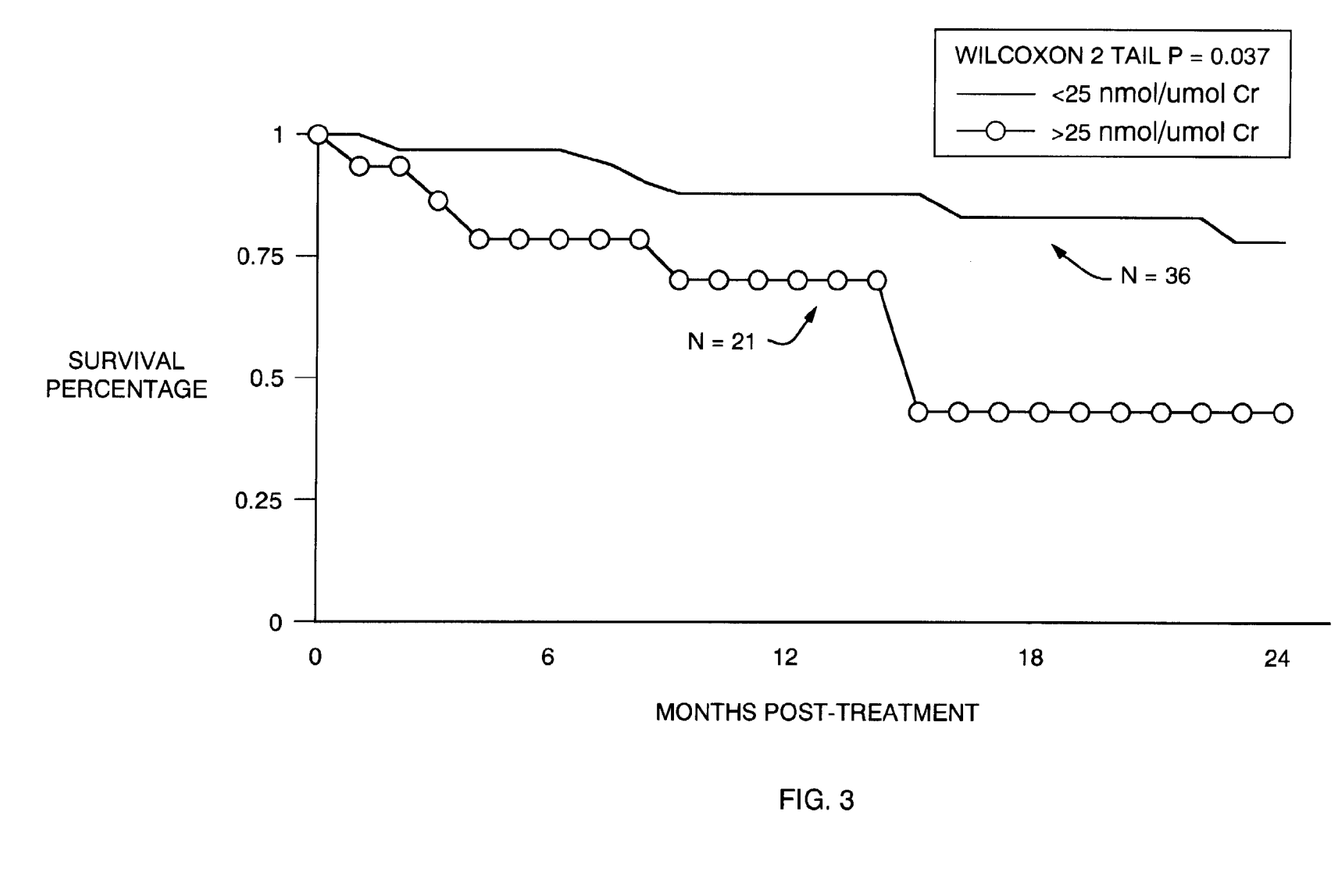
FIG. 3. Midgrade glioma survival and 1-methyladenosine levels.

Pseudouridine and 1-methyladenosine levels were significantly elevated in both Glm and Mng as compared to HC (FIG. 1). FIG. 1A depicts modified nucleoside levels as means±SEM and FIG. 1B demonstrates the range of the MN values. The mean pseudourindine levels are elevated in the glioblastoma (GBN, n=52) and meningioma (MEN, n=52) tumor groups as compared to the healthy volunteer (HC, n=20) and non-tumor craniotomy (CC, n=46) controls. The mean 1-methyladenosine levels are elevated in all three tumor groups in the CC group compared to the HC group. However, due to the broad range of levels observed in all groups, elevations of 1-methyladenosine were not statistically significant.

7-methylinosine was significantly elevated in Mngs as compared to NTC. 7-methylinosine and 1-methyladenosine were both elevated in high-grade gliomas (n=28) as compared to medium-grade gliomas (III–IV, n=14). In the Mng tumor group, 7-methylinosine was significantly elevated in females (n=14) as compared to males (n=9). Interestingly, a correlation between the tumor volumes and the levels of any of the MNs was not found in any of the tumor groups.

No differences in pseudouridine or 1-methyladenosine were found with respect to gender or age in Glm, Mng or controls, but 7-methylinosine levels were found to decrease with increasing age.

These results suggest that the characterization and quantification of urinary MNs is useful in the diagnosis and treatment of brain tumors. Furthermore, the data support the hypothesis that it is altered tumor RNA metabolism and not tumor cell proliferation that is responsible for the elevations of MNs in brain tumor patients.

EXAMPLE 2

Differentiation of "Poor Responders" and "Good Responders" by Measurement of 1-Methyladenosine Levels The pseudouridine, 7-methylinosine and 1-methyladenosine levels of the glioblastoma patient group analyzed in Example 1 were divided into two subgroups: high excretors (those patients having levels above one standard deviation above the mean of the healthy control ("HC") group) and low excretors (those patients having levels below one standard deviation below the mean of the HC group). The values were then plotted against patients' survival from the time of treatment. The patients of the 1-methyladenosine high excretor glioblastoma (GBM) group (n=31) were found to have significantly lower survival rates (Wilcoxon two-tail p=0.0167) than the low excretors (n=23). The patients of the 1-methyladenosine high excretor midgrade glioma (M-G) group (n=36) were also found to have significantly lower survival rates (Wilcoxon two-tail p=0.037) than the low excretor group (n=21).

The data indicates a correlation between the levels of 1-methyladenosine excretion and prognosis. A patient having a high excretor profile is predicted to have a worse prognosis than a patient having a low excretor profile.

EXAMPLE 3

In vitro Assay for Compounds Capable of Reducing Modified Nucleoside Production

The data suggests that compounds capable of slowing or eliminating modified nucleoside production may be useful for treating a disease such as cancer. The above-described data indicates a correlation between the excretion of a high level of modified nucleosides and poor prognosis. The present invention provides an in vitro assay for the identification of compounds having the ability to decrease modified nucleoside excretion from tumor cells. Compounds identified in such an assay may then be tested in an in vivo model as shown below or administered to a patient for treatment of a disease such as cancer.

Human glioma U373 MG cells are seeded onto a 96-well plate at approximately $10^5$ cells/well in normal media and treated with various concentrations of a compound that may affect modified nucleoside production by the cells. Such a compound may include dibutyrate (available from Sigma Chemicals, St. Louis, Mo.) to which the cells may be exposed at $10^{-10}$ to $10^{-1}$ M concentrations. Modified nucleoside levels are then characterized using procedures reported by Gehrke et al. (*J. Chromatography*, 150: 455–476, 1978). A phenyl-boronate affinity column was used as an initial step to partially purify the ribonucleosides. Modified nucleosides contained in this mixture are then analyzed by reversed-phase high performance liquid chromatography (RP-HPLC) using a 4×300 mm μBONDAPAK column (waters, Milford, Mass.) under the following conditions: buffer, 1% methanol in 0.01M sodium phosphate, pH 5.1; temperature, 25° C.; flow rate, 1 ml/min. Modified nucleosides are identified by retention time using known standards and quantified by peak area integration. A compound is determined to affect modified nucleoside production by the cells if an increase or a decrease of the level of a particular modified nucleoside is detected following exposure of the cells to the compound.

The levels of the various nucleosides released by the cells in the absence or presence of dibutyrate at various concentrations is determined. This information may then be extrapolated to determine the in vivo levels needed to achieve a similar modification of modified nucleoside production in a patient following dibutyrate administration in vivo.

EXAMPLE 4

In vitro Assay for Compounds Capable of Reducing Modified Nucleoside Production by Autologous Tumor Cells Variability between tumor types and between similar tumors in different individuals has been a major obstacle in designing effective therapies. The assay of the present invention may be utilized to specifically characterize a patient's own tumor cells with respect to the affect of compounds on modified nucleoside production by tumor cells removed from a patient. In such a manner, a therapeutic regimen may be specifically tailored to a particular patient's tumor.

Following tumor resection from a patient, the tumor cells are isolated using procedures well known and widely available to one skilled in the art for preparing primary cells for culture. Extratumoral cells and material are carefully removed from the tumor fragment to reduce the likelihood of non-tumor cell contamination. The tumor is minced and the fragments treated with a protease such as trypsin for a period of time sufficient to generate a suspension containing single cells. The suspension is then allowed to stand for a period of time sufficient to allow large fragments to settle. The cells are then isolated and washed in a suitable buffer such as phosphate-buffered saline (PBS). The cells are then plated in 96-well plates at approximately $10^5$ cells/well in normal media and treated with various concentrations of a compound that may affect modified nucleoside production by the cells. Such a compound may include dibutyrate (available from Sigma Chemicals, St. Louis, Mo.) to which the cells may be exposed at $10^{-10}$ to $10^{-1}$ M concentrations.

Modified nucleosides are characterized using procedures reported by Gehrke et al. (*J. Chromatography*, 150: 455–476, 1978). A phenyl-boronate affinity column was used as an initial step to partially purify the ribonucleosides. Modified nucleosides contained in this mixture were then analyzed by reversed-phase high performance liquid chromatography (RP-HPLC) using a 4×300 mm $\mu$BONDAPAK column (waters, Milford, Mass.) under the following conditions: buffer, 1% methanol in 0.01M sodium phosphate, pH 5.1; temperature, 25° C.; flow rate, 1 ml/min. Modified nucleosides were identified by retention time using known standards and quantified by peak area integration. These values were then normalized according to each patient's creatine concentration (Sigma Diagnostics Creatinine Kit; Sigma Chemicals, St. Louis, Mo.).

Those compounds having the ability to alter the patient's tumor cell modified nucleoside production patterns are then considered for administration to the patient. In such a manner, certain compounds having the ability to alter autologous tumor cells of a patient may be effectively utilized to treat the patient and prevent tumor recurrence.

EXAMPLE 5

In vivo Model for Detecting Compounds Having the Ability to Alter Tumor Cell Modified Nucleoside Excretion To determine the effectiveness of a chemotherapeutic regimen in treating a particular type of cancer, the concentration of three modified nucleosides (pseudouridine, 7-methylinosine, and 1-methyladenosine) in the urine of multiple rats is measured prior to innoculation with tumor cells. Urine is collected from the patient prior to treatment with a specific chemotherapeutic, radioactive or immunological treatment protocol. The urine is stored at −20° C. Modified nucleosides are characterized using procedures reported by Gehrke et al. (*J. Chromatography*, 150: 455–476, 1978). A phenyl-boronate affinity column is used as an initial step to partially purify the ribonucleosides. Modified nucleosides contained in this mixture are then analyzed by reversed-phase high performance liquid chromatography (RP-HPLC) using a 4×300 mm $\mu$BONDAPAK column (waters, Milford, Mass.) under the following conditions: buffer, 1% methanol in 0.01M sodium phosphate, pH 5.1; temperature, 25° C.; flow rate, 1 ml/min. Modified nucleosides are identified by retention time using known standards and quantified by peak area integration. These values are then normalized according to each animal's creatine concentration (Sigma Diagnostics Creatinine Kit; Sigma Chemicals, St. Louis, Mo.).

Individual rats are then independently inoculated with $10^6$, $5 \times 10^6$, or $10^7$ tumor cells. One week later, urine is collected from each rat and control rats that have not been inoculated with tumor cells. The concentration of pseudouridine, 7-methylinosine, and 1-methyladenosine is determined and compared to the pre-inoculation levels. Both sets of data are further compared to the levels detected in healthy controls that have not been inoculated with any tumor cells. Treatment with a chemotherapeutic compound is then initiated in certain rats (the "treated" group). Treatment is with a chemotherapeutic compound believed to be effective against the particular tumor type from which the tumor cells were derived.

Urine is collected from each rat (treated and untreated) at seven day intervals and assayed for compared to the previous assays. One month after treatment with the compound has begun, urine is once again collected and assayed for the concentration of pseudouridine, 7-methylinosine, and 1-methyladenosine. The levels of modified nucleoside detected in the urine of each rat is then correlated to tumor size and overall health of the animal. If the amount of modified nucleoside has decreased, this indicates that the particular chemotherapeutic compound is effective for treating the particular tumor type. If the levels of modified nucleoside has increased, this indicates that chemotherapeutic compound is ineffective for treating the particular tumor type. In this manner, the effectiveness of a particular chemotherapeutic regimen against a tumor type can be ascertained.

EXAMPLE 6

Kit for Detection of Modified Nucleosides in a Biological Fluid of a Patient

A kit for detecting modified nucleosides in a biological fluid of a patient is provided herein. The kit comprises a dipstick comprising a solid surface comprising three zones to which are separately bound a monoclonal antibody to psueouridine ($\psi$), 7-methylinosine ($m^7I$), or 1-methyladenosine ($m^1A$). The dipstick is placed into a container comprising urine from either a patient suspected of having a brain tumor or a control sample (i.e., from a patient not suspected of having a tumor) and a labeled antibody specific to psueouridine ($\psi$), 7-methylinosine ($m^7I$), or 1-methyladenosine ($m^1A$). The labeled antibody is conjugated to alkaline phosphatase (specific activity>1400 U/mg) at a 1:1 molar ratio using the one step glutaraldehyde method followed by purification of the antibody conjugate on a diethylaminoethyl SEPHADEX A50 (5 ml) column using a liner gradient (0–1M sodium chloride). Conjugate samples (3.0 ml) are collected and assayed for enzyme activity. The antibody is then diluted to a working concentration.

The dipstick, urine and labeled antibody are exposed to one another for approximately three minutes and inserted into a tube containing substrate solution (5-bromo-4-chloro indoyl phosphate-nitroblue tetrazolium) with shaking. The tube is allowed to stand for three minutes and removed from the tube. Each zone of the dipstick that comprises bound antibody specific to specific to psueouridine ($\psi$), 7-methylinosine ($m^7I$), or 1-methyladenosine ($m^1A$) is observed. The presence of a blue color formation at each zone indicates that specific to psueouridine ($\psi$), 7-methylinosine ($m^7I$), or 1-methyladenosine ($m^1A$) is bound to the dipstick. The levels of the different modified nucleosides in the experimental samples are then compared to that of control samples. In general, an increased or decreased amount of modified nucleoside is detected in the experimental sample as compared to the control samples.

As disclosed herein, the present invention provides the reagents and methodologies for the detection of modified nucleosides for detection of cancer or other conditions wherein increased levels of modified nucleosides results. While a preferred form of the invention has been shown in the drawings and described, since variations in the preferred form will be apparent to those skilled in the art, the invention should not be construed as limited to the specific form shown and described, but instead is as set forth in the claims.

We claim:

1. A method for determining the effectiveness of a treatment regimen for cancer comprising determining the concentration of the modified nucleoside 7-methylinosine in a test sample of bodily fluid of a patient wherein a decreased amount of the modified nucleoside in the test sample relative to the amount of the modified nucleoside detected in a control sample of bodily fluid isolated from the patient prior to treatment indicates that the treatment regimen is effective.

2. The method of claim 1 wherein said cancer is brain cancer.

3. The method of claim 2 wherein said cancer is glioma or meningioma.

4. The method of claim 1 wherein the concentration of the modified nucleosides 1-methyladenosine and 7-methylinosine in the test sample are determined and compared to the amount in the control sample, wherein a decreased amount of the modified nucleosides in the test sample as compared to the control sample indicates the treatment regimen is effective.

5. The method of claim 4 wherein said cancer is brain cancer.

6. The method of claim 5 wherein said cancer is glioma or meningioma.

7. A method for determining the effectiveness of a treatment regimen for brain cancer comprising determining the concentration of the modified nucleoside 1-methyladenosine in a test sample of bodily fluid of a patient wherein a decreased amount of the modified nucleoside in the test sample relative to the amount of the modified nucleoside detected in a control sample of bodily fluid isolated from the patient prior to treatment indicates that the treatment region is effective.

8. The method of claim 7 wherein said cancer is glioma or meningioma.

9. A method for determining the effectiveness of a treatment regimen for treating cancer comprising:
  a) adding to a test sample of bodily fluid of a patient to be treated a first antibody comprising a detectable label and having immunological reactivity to the modified nucleoside 7-methylinosine;
  b) contacting the test sample of step (a) with a solid surface to which a second antibody specific to the modified nucleoside is bound under conditions suitable to the formation of a complex of the modified nucleoside with the first antibody and the second antibody;
  c) detecting the first antibody of the complex; and
  d) comparing the amount of modified nucleoside in the test sample to the amount of the modified nucleoside in a control sample of bodily fluid isolated from the patient prior to treatment;
wherein detection of a lower amount of modified nucleoside in the test sample as compared to the control sample indicates that the treatment regimen is effective.

10. The method of claim 9 wherein said cancer is brain cancer.

11. The method of claim 10 wherein said cancer is glioma or meningioma.

12. The method of claim 9, further comprising detecting the amount of the modified nucleoside 1-methyladenosine in the test sample and comparing the amount to the control sample.

13. The method of claim 12 wherein said cancer is brain cancer.

14. The method of claim 13 wherein said cancer is glioma or meningioma.

15. The method of claim 9 or 12 wherein said solid surface support is a dipstick.

16. The method of claim 9 or 12 wherein the first antibody is labeled with a detectable label selected from the group consisting of $^{125}I$, a fluorometric label, and an enzyme label that causes conversion of a substrate to a colored form.

17. A method for determining the effectiveness of a treatment regimen for treating brain cancer comprising:
  a) adding to a test sample of bodily fluid of a patient to be treated a first antibody comprising a detectable label and having immunological reactivity to 1-methyladenosine;
  b) contacting the test sample of step (a) with a solid surface to which a second antibody specific to a modified nucleoside is bound under conditions suitable to the formation of a complex of the modified nucleoside with the first antibody and the second antibody;
  c) detecting the first antibody of the complex; and
  d) comparing the amount of modified nucleoside in the test sample to the amount of modified nucleoside in a control sample of bodily fluid isolated from the patient prior to treatment;
wherein detection of a decreased amount of modified nucleoside in the test sample as compared to the control sample indicates that the treatment regimen is effective.

18. The method of claim 17 wherein said cancer is glioma or meningioma.

19. The method of claim 17 wherein said solid surface support is a dipstick.

20. The method of claim 17 wherein the first antibody is labeled with a detectable label selected from tic group consisting of $^{125}I$, a fluorometric label, and an enzyme label that causes conversion of a substrate to a colored form.

21. A method for diagnosing cancer comprising determining the concentration of the modified nucleoside 7-methylinosine in a test sample of bodily fluid of a patient suspected of having cancer wherein an increased level of modified nucleoside detected in the test sample relative to a control sample indicates the presence of cancer.

22. The method of claim 21 wherein said cancer is brain cancer.

23. The method of claim 22 wherein said cancer is glioma or meningioma.

24. The method of claim 21, further comprising determining the amount of 1-methyladenosine in the test sample and comparing the amount to that of the control sample.

25. The method of claim 24 wherein said cancer is brain cancer.

26. The method of claim 25 wherein said cancer is glioma or meningioma.

27. A method for diagnosing brain cancer comprising determining the amount of 1-methyladenosine in a test sample of bodily fluid of a patient suspected of having brain cancer wherein an increased amount of modified nucleoside in the test sample relative to a control sample indicates the presence of brain cancer.

28. The method of claim 27 wherein said cancer is a glioma or meningioma.

29. A method for assisting in the diagnosis of cancer comprising:
　a) adding to a test sample of bodily fluid of a patient a first antibody comprising a detectable label and having immunological reactivity to 7-methylinosine;
　b) contacting the test sample of step (a) with a solid surface to which a second antibody specific to a modified nucleoside is bound under conditions suitable to the formation of a complex of said modified nucleoside with the first antibody and the second antibody;
　c) detecting the first antibody of the complex; and
　(d) comparing the amount of modified nucleoside detected in the test sample to a control sample;
wherein detection of modified nucleoside in the test sample at an amount greater than that observed in the control sample indicates the presence of cancer.

30. The method of claim 29 wherein said cancer is a brain cancer.

31. The method of claim 30 wherein said cancer is glioma or meningioma.

32. The method of claim 29, further comprising determining the amount of 1-methyladenosine in the test sample and comparing the amount to that of the control sample.

33. The method of claim 32 wherein said cancer is brain cancer.

34. The method of claim 33 wherein said cancer is glioma or meningioma.

35. The method of claim 29 or 32 wherein said solid surface support is a dipstick.

36. The method of claim 29 or 32 wherein the first antibody is labeled with a detectable label selected from the group consisting of $^{125}$I, a fluorometric labels, and an enzyme label that causes conversion of a substrate to a colored form.

37. A method for assisting in the diagnosis of brain cancer comprising:
　a) adding to a test sample of bodily fluid of a patient a first antibody comprising an detectable label having immunological reactivity to 1-methyladenosine;
　b) contacting the test sample of step (a) with a solid surface to which a second antibody specific to a modified nucleoside is bound under conditions suitable to the formation of a complex of said modified nucleoside with the first antibody and the second antibody;
　c) detecting the first antibody of the complex; and
　d) comparing the amount of modified nucleoside detected in the test sample to that of a control sample;
wherein detection of modified nucleoside in the test sample at an amount greater than that observed in the control sample indicates the presence of cancer.

38. The method of claim 37 wherein said cancer is glioma or meningioma.

39. The method of claim 37 wherein said solid surface support is a dipstick.

40. The method of claim 37 wherein the first antibody is labeled with a detectable label selected from the group consisting of $^{125}$I, a fluorometric label, and an enzyme label that causes conversion of a substrate to a colored form.

* * * * *